(12) United States Patent
Takabe

(10) Patent No.: US 6,812,338 B2
(45) Date of Patent: Nov. 2, 2004

(54) PEROXISOMAL ASCORBATE PEROXIDASE GENE INDUCED BY HIGH TEMPERATURE STRESS AND A TRANSGENIC PLANT EXHIBITING THERMOTOLERANCE

(75) Inventor: Tetsuko Takabe, Nagoya (JP)

(73) Assignee: Nagoya University, Nagoya (JP)

( * ) Notice: Subject to any disclaimer, the term of this patent is extended or adjusted under 35 U.S.C. 154(b) by 44 days.

(21) Appl. No.: 09/870,501

(22) Filed: Jun. 1, 2001

(65) Prior Publication Data
US 2002/0100081 A1 Jul. 25, 2002

(30) Foreign Application Priority Data
Jun. 9, 2000 (JP) ......................... 2000-172850

(51) Int. Cl.⁷ .................... C12N 15/29; C12N 15/82
(52) U.S. Cl. ........................ 536/23.6; 800/289
(58) Field of Search ................. 536/23.6; 800/289

(56) References Cited

PUBLICATIONS

Rhoads et al. Regulation of cyanide–resistant alternative oxidase of plant mitochondria. J. Biol. Chem., Nov. 1998, vol. 273, No. 46, pp. 30750–30756.*

Bunkelmann et al., *Gossypium hirsutum* ascorbate peroxidase mRNA, GenBank Accession No. U37060, Apr. 23, 1997.*

Bunkelmann et al., Ascorbate Peroxidase, *Gossypium hirsutum*, SPTREMBL Accession No. Q38780, Nov. 1, 1996.*

Bunkelmann et al., "Ascorbate Peroxidase: A Prominent Membrane Protein in Oilseed Glyoxysomes," Plant Physiology, 1996, pp 589–598, vol. 110, No. 2, USA XP–002225033.

Wing et al., "Development of a Genetically and Physically Anchored EST Resource for Barley Genomics," Oct. 18, 2000, unpublished, Database accession No. BF065877 XP–002225034.

* cited by examiner

*Primary Examiner*—David T. Fox
*Assistant Examiner*—Cynthia Collins
(74) *Attorney, Agent, or Firm*—Burns, Doane, Swecker & Mathis, L.L.P.

(57) ABSTRACT

This invention provides a novel method to render thermotolerance to a plant. In the concrete, this method provides peroxisomal ascorbate peroxidase gene of barely, a novel gene induced by high temperature stress. Moreover, this invention provides a transgenic plant exhibiting resistance to high-temperature stress, produced by incorporating said gene.

2 Claims, 9 Drawing Sheets

```
CTTCTAGGGTCGTCCGCGATGGCGGCTCCGGTGGTGGACGCCGAGTACCTGCGCCAGGTC
                M  A  A  P  V  V  D  A  E  Y  L  R  Q  V
GACAGGGCGCGCCGCGCCTTCCGTGCCCTCATCGCCTCCAAGGGATGCGCCCCCATCATG    120
 D  R  A  R  R  A  F  R  A  L  I  A  S  K  G  C  A  P  I  M     34
CTCCGCCTCGCATGGCATGATGCTGGCACCTATGATGTGAACACAAGAACTGGTGGTGCA
 L  R  L  A  W  H  D  A  G  T  Y  D  V  N  T  R  T  G  G  A
AATGGTTCAATTAGATACGAGGAAGAGTACACCCATGGTTCAAATGCTGGCTTAAAAATT    240
 N  G  S  I  R  Y  E  E  E  Y  T  H  G  S  N  A  G  L  K  I     74
GCTATTGATCTCCTTGAGCCTATTAAAGCGAAGCATCCAAAGATTACATATGCAGACCTT
 A  I  D  L  L  E  P  I  K  A  K  H  P  K  I  T  Y  A  D  L
CATCAGCTTGCCGGAGTAGTTGCAGTTGAAGTCACCGGGGGTCCAACCGTTGAGTTCATC    360
 H  Q  L  A  G  V  V  A  V  E  V  T  G  G  P  T  V  E  F  I    114
CCTGGAAGACGTGATTCGTCAGTTTGTCCCCGTGAAGGACGCCTTCCTGATGCTAAGAAA
 P  G  R  R  D  S  S  V  C  P  R  E  G  R  L  P  D  A  K  K
GGTGCACCACATCTAAGGGACATCTTTTATCGAATGGGGTTAACAGACAAAGATATTGTA    480
 G  A  P  H  L  R  D  I  F  Y  R  M  G  L  T  D  K  D  I  V    154
GCACTATCTGGGGGGCACAGCCTGGGAAAGCGCATCCTGAAAGGTCTGGGTTTGACGGT
 A  L  S  G  G  H  S  L  G  K  A  H  P  E  R  S  G  F  D  G
GCATGGACTCGTGACCCTCTGAAATTTGACAACTCATACTTTCTTGAGCTACTGAAGGGG    600
 A  W  T  R  D  P  L  K  F  D  N  S  Y  F  L  E  L  L  K  G    194
GAATCTGAGGGTCTTCTGAAGCTCCCTACTGATAAGGCATTGTTGGATGATCCTGAATTT
 E  S  E  G  L  L  K  L  P  T  D  K  A  L  L  D  D  P  E  F
CGACGCTATGTGGAGCTTTATGCAAAGGATGAGGATGTTTTCTTCAAGGACTACGCTGAA    720
 R  R  Y  V  E  L  Y  A  K  D  E  D  V  F  F  K  D  Y  A  E    234
TCACACAAAAAACTTTCTGAACTTGGCTTCACACCACGGAGCAGTGGCCCAGCATCTACA
 S  H  K  K  L  S  E  L  G  F  T  P  R  S  S  G  P  A  S  T
AAATCAGATGTTTCAACTGCTGTT<u>GTACTTGCACAGAGTGCAGTCGGGGTAGCAGTTGCT</u>    840
 K  S  D  V  S  T  A  V  <u>V  L  A  Q  S  A  V  G  V  A  V  A</u>   274
<u>GCAGCTGTAGTTATCGCGGGCTACCTGTAC</u>GAAGCTTCCAAGAGGAGCAAGTAAGGGGTT
 <u>A  A  V  V  I  A  G  Y  L  Y</u>  E  A  S  K  R  S  K  *        291
CGTGAGTTCTTGGATGACATTCCCTTATTTAGTAAGTATCAAGTTATTATTCTAAAAAAA    960
TAAGTGCCAAGTGCAAATAACAGAACTCTAGTGATGAACAACCAACAGTAGTCTCAAAAT
ATTTCATACATTCTTGAGGACATCTCCTTCATATATATACATCATACTTGAATAAAAAAA   1080
AAAAAAAAA   1089
```

FIG. 3

| | |
|---|---|
| pAPX | MAAPVVDAEYLRQVDRARRAFRALTASKGCAPIMLRLAWHDAGTYDVNTRTGGA |
| gAPX | MAFPVVDTEYLKEIDKARRDLRALIALAKNCAPIMLRLAWHDAGTYDVSTKTGGP |
| APX3 | MAAPIVDAEYLKEITKARELRSLIANKNCAPIMLRLAWHDAGTYDAQSKTGGP |

| | |
|---|---|
| pAPX | NGSIRYEEEYTHGSNAGLKIAIDLLEPIKAKHPKITYADLHQLAGVVAVEVTGG |
| gAPX | NGSIRNEEEYTHGANSGLKIAIDFCEEVKAKHPKITYADLYQLAGVVAVEVTGG |
| APX3 | NGSIRNEEEYTHGANSGLKIAIDLCEGVKAKHPKITYADLYQLAGVVAVEVTGG |

| | |
|---|---|
| pAPX | PTVEFIPGRRDSSVCPREGRLPDAKKGAPHLRDIFYRMGLTDKDIVALSGGHSL |
| gAPX | PTIDFVPGRKDSNICPREGRLPDAKRGAPHLRDIFYRMGLSDKDIVALSGGHSL |
| APX3 | PDIVFVPGRKDSNVCPKEGRLPDAKQGFQHLRDVEYRMGLSDKDIVALSGGHTL |

| | |
|---|---|
| pAPX | GKAHPERSGFDGAWTRDPLKFDNSYFLELLKGESEGLLKLPTDKALLDDPEFRR |
| gAPX | GRAHPERSGFDGPWTNEPLKFDNSYFLELLKGESEGLLKLPTDKALLDDPEFRK |
| APX3 | GRAHPERSGFDGPWTQEPLKFDNSYFVELLKGESEGLLKLPTDKTLLEDPEFRR |

| | |
|---|---|
| pAPX | YVELYAKDEDVFFKDYAESHKKLSELGFTPRSSGPASTKSDVSTAVVLAQSAVG |
| gAPX | YVELYAKDEDAFFRDYAESHKKLSELGFTPTSARSKVMVKD-ST-V-LAQGAVG |
| APX3 | LVELYAKDEDAFFRDYAESHKKLSELGFNPNSSAGKA-VAD-STI--LAQSAFG |

| | |
|---|---|
| pAPX | VAVAAAVVIAGVLYEASKRSK |
| gAPX | VAVAAAVVILSVFYEVRKRMK |
| APX3 | VAVAAAVVAFGYFYEIRKRMK |

Wild
type  pAPX1  pAPX2  pAPX3  pAPX5  pAPX7  pAPX8

Wild type    pAPX1    pAPX2    pAPX3    pAPX5

PEROXISOMAL ASCORBATE PEROXIDASE GENE INDUCED BY HIGH TEMPERATURE STRESS AND A TRANSGENIC PLANT EXHIBITING THERMOTOLERANCE

BACKGROUND OF THE INVENTION

1. Field of the invention

This invention relates to peroxisomal ascorbate peroxidase gene from barley, which is a novel gene induced by high temperature stress and a transgenic plant exhibiting improved thermotolerance produced by incorporating said gene.

2. Description of Related Art

Food crisis is expected to occur in the near future, caused by increase of population and alteration of environment. Therefore, in order to cope with the problem, there is a great demand on development of a agricultural technique that enables efficient production of crops. The amount of agricultural production tends to be effected by various environmental stresses. It reserves to be a serious problem in the field of agriculture. Therefore production of a plant, exhibiting resistance to various environmental stress, is needed. Especially, anathermal of the earth is a serious problem. Therefore, production of a plant having improved thermotolerance reserves to be great value.

Until now, for the production of a transgenic plant having improved thermotolerance by a genetic engineering technique, a gene encoding heat shock protein, induced by high-temperature stress, have been utilized for such purpose. Furthermore in order to attain above purpose, small amount of glycine betaine, which is a suitable solute to prevent enzyme denaturation under heat stress, was also biosynthesized in a plant body. Moreover, it has been recognized that genes, involved in decomposing of active oxygen molecules, are important for resistance to environmental stress. Using such genes, resistance to photo-oxidation injury, resistance to salt stress or resistance to aridity stress was rendered to a plant by incorporating said gene involved in resistance to environmental stress. Despite of it, there have been no report describing on imparting of thermotolerance, achieved by incorporating genes involved in decomposition of active oxygen molecules described above.

SUMMARY OF THE INVENTION

The inventor has remarked importance of genes involved in decomposition of active oxygen molecules and challenged on imparting thermotolerance to a plant by incorporating a gene involved in decomposition of active oxygen molecules, not by conventional techniques of incorporating a gene encoding heat shock protein. That is, it is an object of this invention to develop a novel technique which can impart thermotolerance to a plant by incorporating a gene involved in defense to oxidative stress. In the concrete, it is an object of this invention to obtain a novel gene useful for such purpose and determine base sequence of the gene.

High temperature stress is one of the main factors constraining the growth and productivity of plants. Living organisms respond rapidly to high temperatures by metabolic changes that involve complex reprogramming of cellular activities. These changes must help to protect the essential structures and functions of cells against damage caused by the stress. It is known that heat shock can result in an oxidative stress, which induces genes involved in the oxidative stress defense. Under heat stress, excessive active oxygen species (AOS) such as superoxide radicals, hydrogen peroxide, and hydroxyl radicals are formed which cause oxidative damage of cell constituents.

A major hydrogen peroxide detoxifying system in plant chloroplast and cytosol is the so-called ascorbate glutathione cycle, in which APXs (ascorbate peroxidases) are the key enzymes. APX is believed to be involved in the detoxifying of photoproduced hydrogen peroxide. APX activity has been shown to increase in response to a number of stress conditions, such as drought, air pollution, high light intensity combined with chilling, UV light and deficiency in microelements.

So far, several different protein isoforms are known, those are two soluble cytosolic forms, and two chloroplast forms, one of which is stromal and the other thylakoid bound. Recently, several isoforms bound to membranes of glyoxysomes and peroxisomes were reported. Recently peroxisomal type ascorbate peroxidase was cloned from cotton (Bunkelmann & Trelease (1996) Plant Physiology 110, 589–598), Arabidopsis (Zhang et al. (1997) Plant Molecular Biology 34, 967–971) and spinach (Ishikawa et al. (1998) Plant and Cell Physiology 39, 23–34). Incidentally, novel gene according to this invention was obtained independent to known sequences described above.

Peroxisome, with glyoxysome, is an micro-organella exhibiting function, specialized to oxidative reaction utilizing molecular oxygen. These organellas described above are totally designated to microbody. The name of peroxisome is originated from production of hydrogen peroxide catalyzed by an enzyme localized at the organella. In the enzyme reaction, hydrogen atom is depleted from substrate, which is an organic compound, utilizing molecular oxygen. Moreover, catalase also exists in peroxisome. Hydrogen peroxide, generated by the reaction described above, is utilized for oxidation of compounds such as phenols, formaldehyde and alcohols by so-called "peroxidative reaction". Such oxidative reaction is involved in detoxification of harmful molecules, accordingly exhibiting great importance especially in cells of liver or kidney.

Under various stress conditions, generation of hydrogen peroxide increases in microbody and the generated hydrogen peroxide diffuses into cytosol. The peroxisomal type ascorbate peroxidase of this invention is assumed to be bound outside of peroxisome membrane, operating to protect cells from injury by decomposition of hydrogen peroxide. Therefore, peroxisomal type ascorbate peroxidase of this invention would enable rapid deletion of active oxygen species generated in peroxisome before transition to cytosol, which could not be achieved by conventional ascorbate peroxidase of cytosolic form or chloroplast form.

These and other features and advantages of this invention will become apparent upon a reading of the detailed description and drawings.

BRIEF EXPLANATION OF THE DRAWINGS

The file of this patent contains at least one drawing executed in color. Copies of this patent with color drawing (s) will be provided by the Patent and Trademark Office upon request and payment of the necessary fee.

FIG. 2 is a figure showing base sequence and deduced amino acid sequence of peroxisomal ascorbate peroxidase from barley.

FIG. 3 is a figure showing comparison of amino acid sequences of peroxisomal ascorbate peroxidase from barley, cotton and *Arabidopsis*.

DETAILED DESCRIPTION OF THE INVENTION

Therefore, the inventors have isolated peroxisomal ascorbate peroxidase gene from cDNA library prepared from barely leaf using the technique of differential display method. Moreover, the inventors have determined base sequence of the gene. As described above, all of peroxisomal ascorbate peroxidases cloned so far are those derived from dicotyledonous plants, such as cotton, *Arabidopsis* and spinach. The peroxisomal ascorbate peroxidase of this invention provides the first example of cloning peroxisomal ascorbate peroxidase derived from monocotyledonous plant. The differential display method utilized in this invention comprises the steps of RT-PCR using one short primer, separating by sequence gel and subsequently analyzing the obtained sequence. Here, said short primer consists of arbitrary sequence, exhibiting high frequency expression in the gene of eukaryotic cell. It should be noted that this method enables detection with high sensitivity, which is the advantage of this method. The base sequence of the gene of this invention was thus determined. Moreover, it was exhibited that expression of the gene was induced under high-temperature stress. Moreover, improved thermotolerance was also exhibited when the gene was over expressed in *Arabidopsis thaliana*.

This invention relates to peroxisomal ascorbate peroxidase gene originated from barley, consisting of a base sequence referred to as base numbers from 1 to 1089 shown in SEQ ID NO: 2 in the sequence list. Said peroxisomal ascorbate peroxidase gene is involved in thermotolerance of a plant and its expression is induced by high-temperature stress.

According to technique of gene recombination, artificial modification can be achieved at a specific site of basic DNA, without alteration or with improvement of basic characteristic of said DNA. Concerning a gene having native sequence provided according to this invention or modified sequence different from said native sequence, it is also possible to perform artificial modification such as insertion, deletion or substitution to obtain gene of equivalent or improved characteristic compared with said native gene. Moreover, a gene with such mutation is also included in the range of this invention. That is, the gene, consisting of a base sequence hybridizes with said base sequence shown in SEQ ID NO: 2 in the sequence list under stringent condition, means a gene in which 20 or less, preferably ten or less, and more preferably five or less bases of the sequence is deleted, substituted or added to the base sequence shown in SEQ ID NO: 2 in the sequence list. Moreover, such gene exhibits homology 70% or more, preferably 80% or more and still preferably 90% or more with the base sequence shown in SEQ ID NO: 2 in the sequence list. In addition, such gene hybridizes with the base sequence shown in the SEQ ID NO: 2 in the sequence list under stringent condition. Such gene is also within the range of this invention so far as it exhibits the characteristic of peroxisomal ascorbate peroxidase gene, being induced by high-temperature stress.

Furthermore, this invention relates to peroxisomal ascorbate peroxidase polypeptide originated from barley, consisting of an amino acid sequence referred to as amino acid numbers from 1 to 291 shown in SEQ ID NO: 1 in the sequence list. The polypeptide is encoded by open reading frame portion of the base sequence indicated by SEQ ID NO: 2 in the sequence list. The polypeptide consisting of an amino acid sequence in which a part of said polypeptide referred to as amino acid sequence shown in SEQ ID NO: 1 is deleted, substituted or added with another amino acid sequence means a polypeptide in which 20 or less, preferably ten or less, and more preferably five or less amino acids of the sequence is deleted, substituted or added to the amino acid sequence shown in SEQ ID NO: 1 in the sequence list. Moreover, such polypeptide exhibits homology 70% or more, preferably 80% or more and still preferably 90% or more with the amino acid sequence shown in SEQ ID NO: 1 in the sequence list. Such polypeptide is also within the range of this invention so far as it exhibits characteristic as peroxisomal ascorbate peroxidase polypeptide, being encoded by a gene induced by high-temperature stress.

A method to transform a plant by incorporating peroxisomal ascorbate peroxidase gene into a plant, and a transgenic plant produced by incorporation of said peroxisomal ascorbate peroxidase gene are also within the range of this invention. The peroxisomal ascorbate peroxidase gene of this invention is a gene induced by high-temperature stress and it is involved in self defense mechanism of a plant. Therefore, resistance to high-temperature stress can be rendered to a plant by incorporating said gene into a plant. The example of plants, preferred as a target plant, to which said gene induced by salt stress of this invention is incorporated, may include monocotyledonous plants, such as barely, wheat, lily, rice, maize and asparagus as well as dicotyledonous plants, such as *Arabidopsis*, tobacco, carrot, soybean, tomato and potato.

A conventional method known in this art, as a method to produce a transformant, can be utilized. A vector available in this invention may include a plasmid vector, such as pBI121 utilized in following embodiment and pBI221, but not limited to them. Such vector can be incorporated into an *Agrobacterium* strain, then the target plant can be infected by said *Agrobacterium* to produce a transgenic plant. Moreover, transformed individuals can be selected using kanamycin resistance, incorporated into the plasmid, as a marker of selection. Furthermore, a seed from such transgenic plant can be obtained. The method to incorporate said plant gene of this invention is not limited to *Agrobacterium* method and other methods, such as particle gun method and electroporation method, can be also utilized for incorporation of the gene.

Embodiment
(Plant Material)

Barley (*Hordeum vulgare* L. Haruna-nijyo) plants were grown hydroponically with 1,000 times diluted Hyponex in tap water in a growth chamber under a light period of 13 h, 25° C., at 100 $\mu$mol m$^{-2}$s$^{-1}$, and a dark period of 11 h, at 23° C. with the humidity at 70% for 2–3 weeks. For salt stress treatment, the NaCl concentration of the culture medium was raised in 100 mM steps every second day until 300 mM, and kept there for 2 d. Heat stress was conducted in the light by exposing the whole plants to 37° C. with the humidity at 70% in a chamber for 24 h. Abscisic acid (ABA) was added directly into the culture solution at 50 $\mu$M and hydrogen peroxide at 1.5% (approximately 440 mM).

(Differential Display)

Poly (A$^+$) RNA was prepared by using an oligo (dT)-cellulose column (Pharmacia). First-strand cDNA was synthesized by reverse transcriptase using random primers (6mer). PCR reactions were carried out as described previously by (Muramoto et al. Photosynthesis Mechanisms and Effects volume IV (eds Garab), pp.3043–3046. Academic Publishers). Salt-stress induced PCR fragments were cloned into a pGEM-T vector (Promega). The DNA sequences were determined by the dye-primer sequencing method on a DNA sequencer (ABI: 373A). A partial fragment encoding part of APX was obtained, according to the BLAST homology searching.

(Cloning and Sequencing of Barley Gene for pAPX)

A complementary DNA library of salt-stressed barley leaves was prepared as described previously (Ishitani et al. (1995) Plant Molecular Biology 37, 307–315). The library was screened by the PCR fragment labeled with [$\alpha$-$^{32}$P] dCTP using a Megaprime DNA labeling (Amersham). Positive clones were excised from the ZAPII vector into the pBluescript plasmid according to the manufacturer's protocol. The DNA sequences were determined as described above.

(Southern and Northern Blot Analysis)

Genomic DNA was isolated from barley leaves according to the conventional method. Genomic DNA was digested with restriction enzymes, BamHI, BglII, EcoRI, EcoRV, and HindIII, and separated on 0.8% agarose gel. After transferring to a nylon membrane (Hybond-N$^+$, Amersham), hybridization was carried out in a solution containing 6×SSC, 5×Denhardt's solution, 0.1% SDS and 0.1 mg/ml denatured herring sperm DNA. The membrane was washed in 2×SSC, 0.1% SDS, and then in 1×SSC, 0.1% SDS, and further in 0.1×SSC, 0.1% SDS. All hybridization and washing were performed at 65° C. Twenty-day-old plants were exposed to stress conditions as described above, and then harvested and stored at −80° C. for RNA extraction. RNA was isolated by ATA (aurintricarboxylic acid) method. Twenty $\mu$g of total RNA were separated on 1.2% agarose gel containing 0.66 M formaldehyde and transferred to a nylon membrane (Hybond-N, Amersham). All hybridization and washing were done at 65° C. The signals were analyzed with a BAS2000 Bioimage Analyzer (Fuji).

(Construct of Expressing Plasmid and Transformation)

Figure 1:
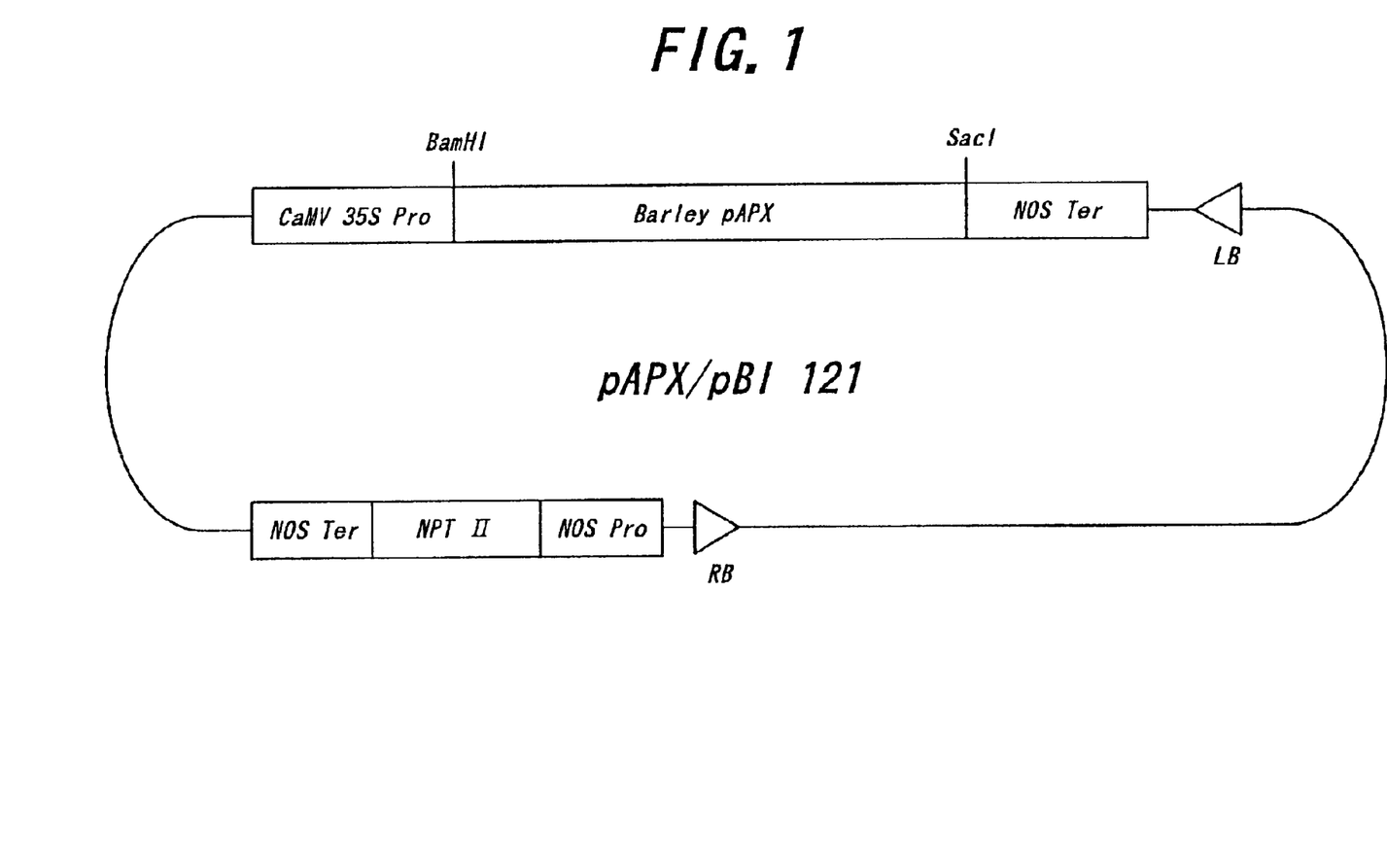
FIG. 1 is a schematic view showing construction of pAPX over expression vector used to transform *Arabidopsis thaliana*.

The pAPX sequence encoding the full-length pAPX protein was ligated into the binary vector of pBI121 with the replacement of the GUS fragment and under the control of the CaMV 35S promoter (FIG. 1). In FIG. 1, RB and LB indicates right border sequence and left border sequence, respectively. The plasmid was then introduced into *Agrobacterium tumefaciens* by electroporation. pAPX was introduced into *Arabidopsis thaliana* ecotype Columbia mediated via *Agrobacterium* by in planta transformation (Shimamoto K. and Okada K. ed. Experimental Protocol for Model Plants: Rice and Arabidopsis, SYUJUNSYA Co. Ltd, Tokyo, 1996). After harvesting, the seeds were plated on kanamycin-containing MS (Murashige & Skoog) medium and the kanamycin-resistant plants (T1) were collected. The transformed seedlings were transferred into vermiculite-containing pots watering with 1,000 times diluted Hyponex in tap water and grown under routine conditions for harvesting the T2 seeds.

(Thermotolerance Test with Transgenic Plants)

The seeds of wild type and selected fully homozygous T3 transgenic lines were sown on vermiculite watering with 1,000 times diluted Hyponex in tap water and grown in a growth chamber under a light period of 16 h, 23° C., 100 $\mu$mol m$^{-2}$s$^{-1}$ and dark period of 8 h, 23° C. with the humidity at 50% for 3 weeks. Plants were exposed to 35° C. with the humidity 70% in the growth chamber for 5 d and then transferred to the routine conditions for recovery. After 5 d, the plants were harvested and the fresh weight of the green part and yellow parts were weighed separately. Each experiment was done with five replicates.

(Cloning and Sequencing of pAPX)

By DDRT-PCR (differential display reverse transcription PCR) with a RAPD primer (5'-CTTGAGCGTATT-3'), the inventors detected a DNA fragment that was preferentially amplified from mRNAs prepared from the salt-stressed leaves. After sequencing, this fragment was found to have high homology to APX genes according to BLAST homology searching. Using this fragment as the probe, the inventors subsequently isolated the full-length cDNA clone from a cDNA library prepared from the leaves of salt-stressed barley. The cDNA was 1089 bp in length and contained an open reading frame encoding a predicted polypeptide of 291 amino acids (FIG. 2). In FIG. 2, the transmembrane region was indicated by underline and the characteristic long C-terminal was indicated as italic. Its deduced amino acid sequence had 75.3% homology to that from *Gossypium hirsutum* glyoxysomal APX (gAPX) and 72.1% homology to that from *Arabidopsis thaliana* APX3 (FIG. 3). Both the characteristic long C-terminal part and the transmembrane domain were also found and conserved. So, the isolated clone encodes the peroxisomal type ascorbate peroxidase and we designated it as pAPX.

(Southern Blot Analysis)

Figure 4:
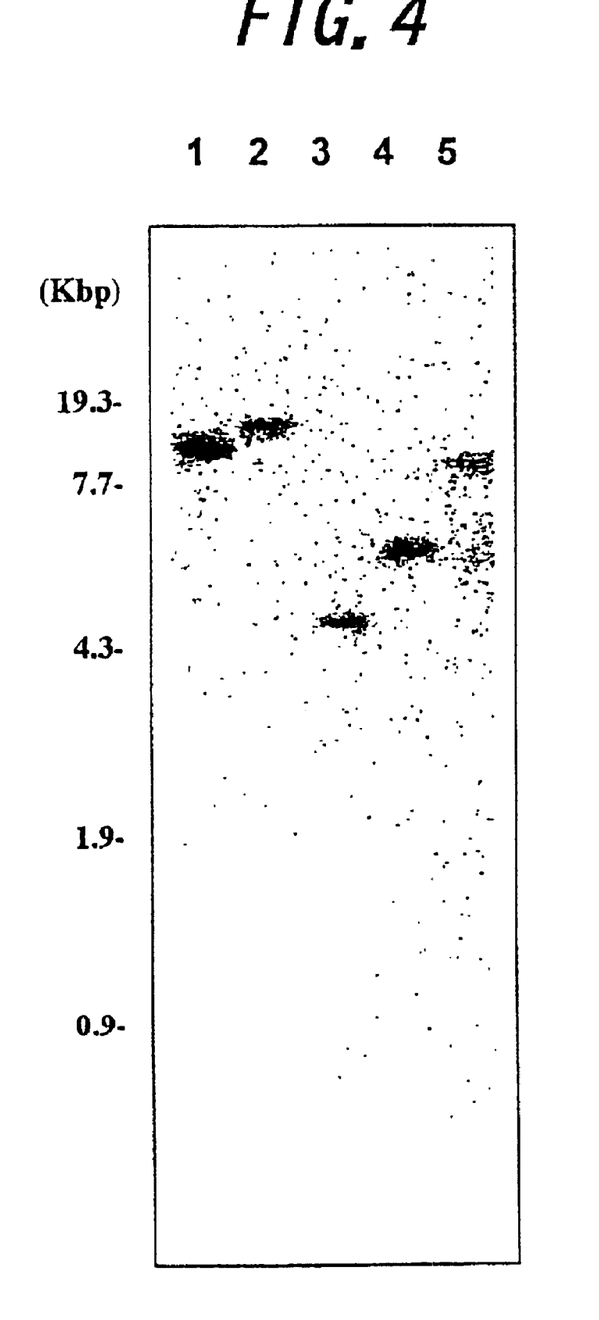
FIG. 4 is a photograph showing Southern blot analysis for pAPX in barley using barley pAPX specific DNA sequence as a probe.

To estimate the copy number of the gene, we carried out Southern blot analysis using 3'-UTR plus 150 base pair (bp) of C-terminal encoding region as a probe. The pAPX cDNA has one internal HindIII restriction site but no site for BamHI, BglII, EcoRI, and EcoRV restriction enzymes. In FIG. 4, lanes 1, 2, 3, 4 and 5 indicate results of digestion by BamHI, BglII, EcoRI, EcoRV and HindIII, respectively. As shown in FIG. 4, under high-stringency condition, only a single band in the BamHI, BglII, EcoRI and EcoRV digests and 2 bands in HindIII digest were detected. This indicates that pAPX was encoded by a single-copy gene in the genome of barley.

(Expression of pAPX Genes Under Heat and Other Stresses)

Figure 5:
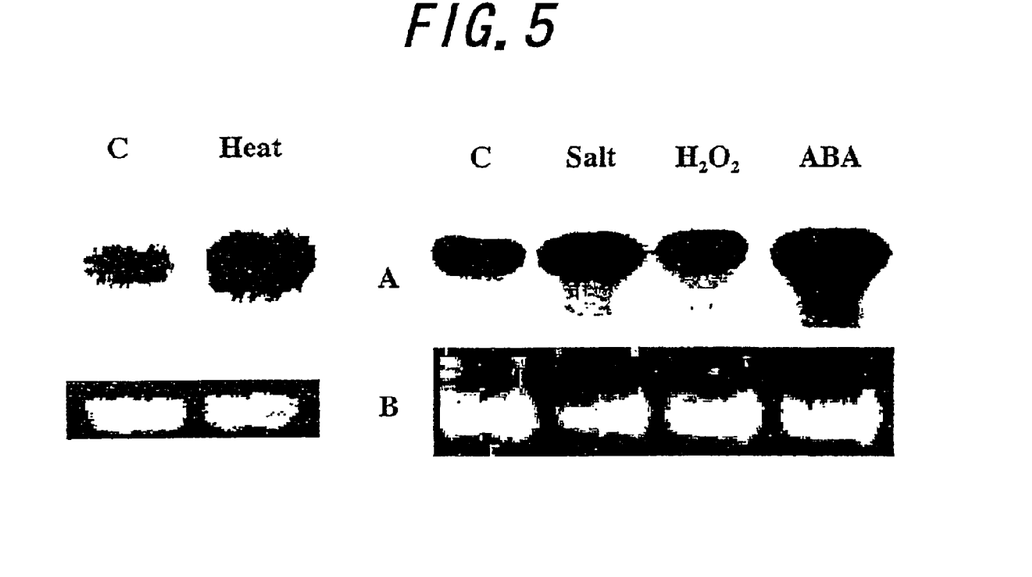
FIGS. 5A and 5B are contained in a photograph which shows Northern blot analysis for pAPX expression in barley induced by heat and other treatments using barley pAPX specific DNA sequence as a probe.

FIG. 5 indicates result of Northern blot analysis of pAPX under various stress. In FIG. 5, samples were prepared from plants grown under normal (C), salinity (300 mM NaCl), ABA-treated (50 $\mu$M) conditions, and heat-stress (37° C., 24 h). In upper photograph A, detection was performed using 3'-UTR of pAPX cDNA plus 150 bps of c-terminal encoding region as a probe. In lower photograph B, 25S rRNA was visualized by EtBr, as a control. RNA blot analysis as a control (FIG. 5) indicated that pAPX transcript level was obviously increased under heat and salt stress. Addition of ABA also caused even higher induction of pAPX gene expression. However, adding hydrogen peroxide directly to the growth medium did not induce its expression.

(Thermotolerance of the Transgenic Arabidopsis Overexpressing pAPX)

Figure 6:
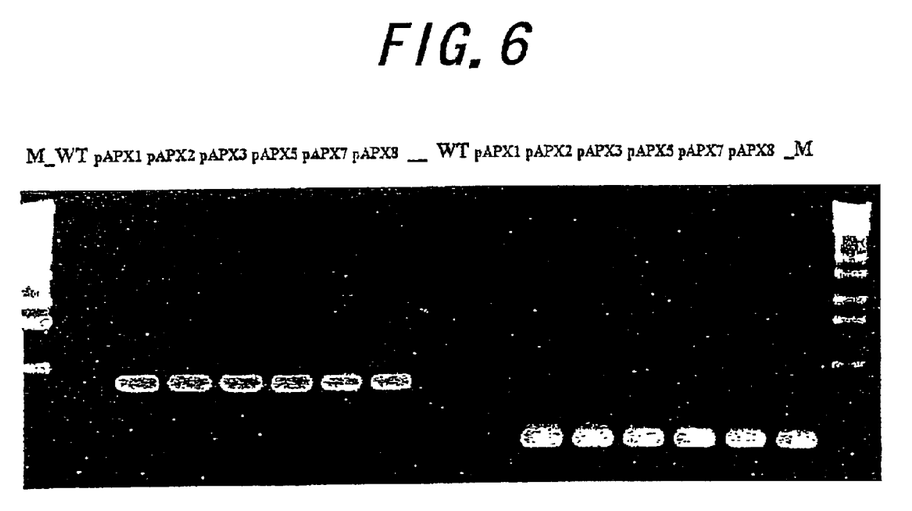
FIG. 6 is a photograph showing PCR analysis of wild-type and transgenic plants for the presence of pAPX transgene.

From the T0 seeds pool (harvested from *Agrobacterium tumefaciens* infected Arabidopsis plants), totally 8 independent transgenic lines (T1) were screened out from kanamycin-containing media. After self-pollinated, T2 progency were plated on kanamycin-containing media again for segregation analyses. According to the segregation analysis, six lines were found to have a single T-DNA insertion. The genomic DNAs were isolated from wild-type and six T2 transgenic lines, then analyzed by PCR using two sets of primer of pAPX representing 131–511 bp and 131–916 bp. The result is shown in FIG. 6. In FIG. 6, PCR products representing pAPX sequence region of 131–916 bp is shown in the left and PCR products representing pAPX sequence region of 131–511 bp is shown in the right. In addition, pAPX1, pAPX2, pAPX3, pAPX5, pAPX7 and pAPX8 indicate each dependent Arabidopsis strains, respectively. No DNA fragment could be amplified from wild-type plants, whereas an expected 380 bp or 785 bp long fragment was amplified from DNAs of all transgenic lines tested (FIG. 6), indicating that these lines contain the pAPX transgene. T3 transgenic lines were produced by self-pollination of T2 again. From these, 50–60 seeds were plated on Kanamycin-containing MS media to select homozygous lines which showed all offspring resistant to kanamycin. Only those homozygous lines were used for further analysis and thermotolerance test.

Figure 7:
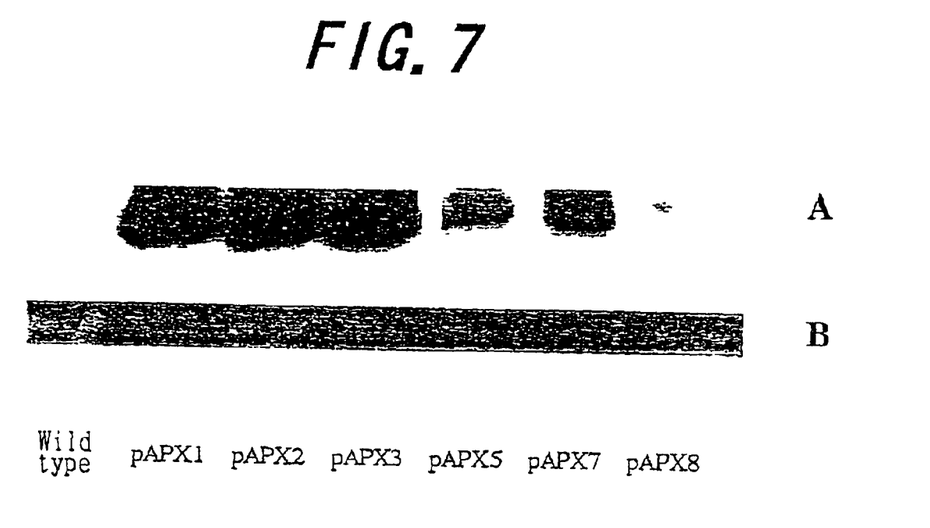
FIGS. 7A and 7B are contained in a photograph which shows Northern blot analysis of wild-type plants and pAPX-overexpressing transgenic plants of T2 generation.

The pAPX transcript level was checked by Northern blot analysis in both the wild type (WT) and transgenic *Arabidopsis thaliana* seedlings. FIG. 7 shows the result of Northern blot analysis of wild type plants and pAPX-overexpressing transgenic plants of T2 generation, using full-length pAPX as the probe. In upper photograph A, detection of transcripts hybridizing with the barely specific pAPX probe was performed on pAPX1, pAPX2, pAPX3, pAPX5, pAPX7 and pAPX8. In lower photograph B, 25S rRNA was visualized by EtBr, as a control. As shown in FIG. 7, the wild-type plants do not contain transcripts hybridizing with the pAPX probe, but all transgenic lines contain abundant pAPX transcript. Among them, lines of pAPX1, pAPX2 and pAPX3 had the highest level, while pAPX5 and pAPX7 were relatively lower. The pAPX expression was very weak in the line pAPX8.

Figure 8:
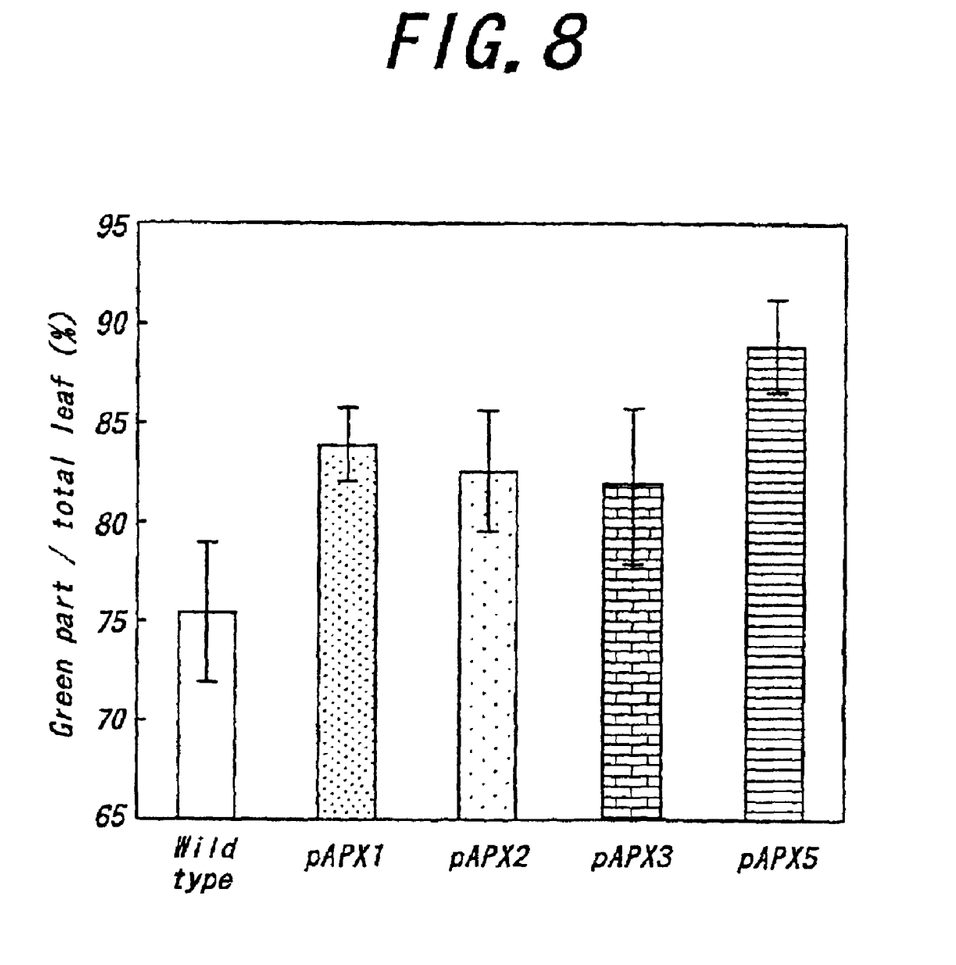
FIG. 8 is a graph showing comparison of wild-type and transgenic pAPX to heat stress, using fresh weight of green part in total leaf as the index.
Figure 9:
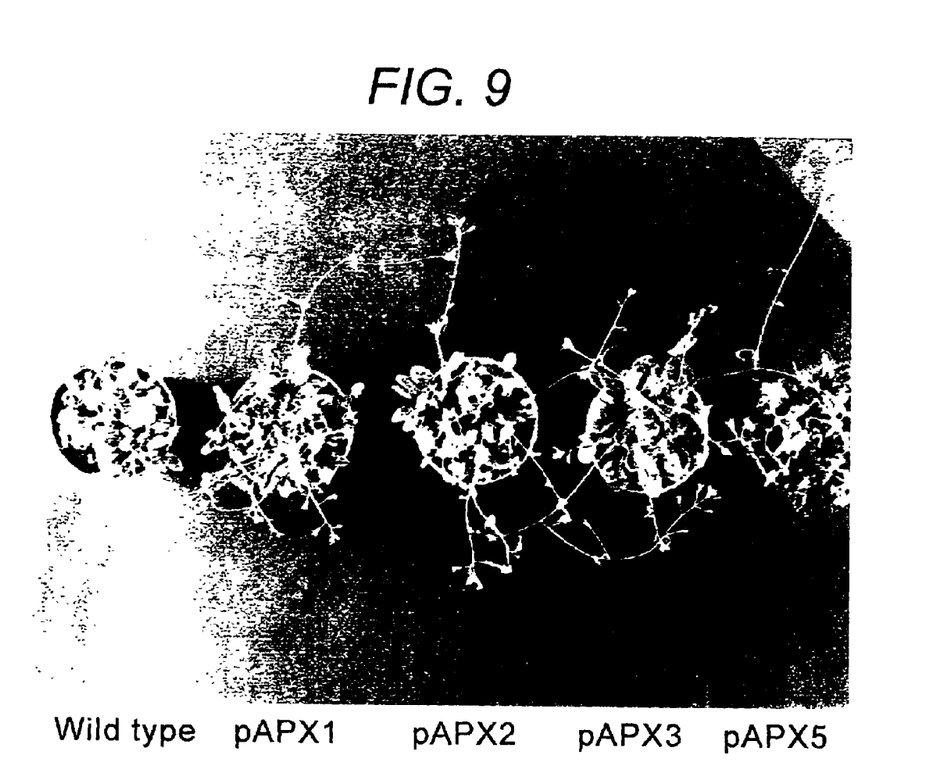
FIG. 9 is a photograph showing comparison of growth between wild-type and transgenic pAPX, after exposure to heat stress.

When 3 weak-old plants were exposed to heat stress, all transgenic lines tend to be more tolerant to high temperature stress than wild type. The percentage of green part over the total in line pAPX5 and pAPX1 were significantly higher (P<0.05) than WT (FIG. 8). However, the thermotolerance is not positively correlated to the pAPX transcript level in the transgenic lines, since line pAPX5 which has lower transcript level was more tolerant to high temperature stress than pAPX1-3 with higher transcript levels. Moreover, FIG. 9 is the photograph exhibiting growth condition of plant bodies of wild type strain and pAPX transformants, after exposure to high temperature stress. Accordingly, it was revealed that transformants expressing suitable amount of pAPX mRNA exhibited significant thermotolerance. This may imply importance of the optimal balance among pAPX and other antioxidant enzymes. FIG. 9 shows that growth of transformed *Arabidopsis* was fairly good even after exposure to high temperature stress, indicating improved thermotolerance of the transformant. Compared with it, growth of wild type strain was damaged as shown in FIG. 9.

This method provides peroxisomal ascorbate peroxidase gene of barely, a novel gene induced by high-temperature stress. This invention also provides a transgenic plant exhibiting resistance to high temperature stress, produced by incorporating said gene. The method of this invention provides a novel technique to render thermotolerance to a plant.

What is claimed is:

1. An isolated nucleic acid sequence selected from the following:
   (a) an isolated nucleic acid sequence consisting of nucleotides 1 to 1089 of SEQ ID NO:2;
   (b) an isolated nucleic acid sequence, wherein no more than 5 nucleotides have been added to, deleted from, or substituted in the isolated nucleic acid of (a); or
   (c) an isolated nucleic acid sequence which hybridizes to the isolated nucleic acid sequence of (a) at 65° C. in a solution containing 6×SSC, 5×Dernhardt's solution, 0.1% SDS, and 0.1 mg/ml denatured herring sperm DNA, followed by washing at 65° C. in 2×SSC, 0.1% SDS; then in 1×SSC and 0.1% SDS; and then in 0.1×SSC and 0.1% SDS; and wherein expression of said isolated nucleic acid sequence is induced by high temperature stress, is derived from barley, and confers thermotolerance to a plant transformed therewith.

2. An isolated nucleic acid sequence encoding a polypeptide selected from the following:
   (a) an isolated nucleic acid sequence encoding amino acids 1 to 291 of SEQ ID NO:1;
   (b) an isolated nucleic acid sequence, wherein no more than 5 amino acids have been added to, deleted from, or substituted in the polypeptide encoded by the isolated nucleic acid of (a); or
   (c) an isolated nucleic acid sequence which hybridizes to the isolated nucleic acid sequence of (a) at 65° C. in a solution containing 6×SSC, 5×Dernhardt's solution, 0.1% SDS, and 0.1 mg/ml denatured herring sperm DNA, followed by washing at 65° C. in 2×SSC, 0.1% SDS; then in 1×SSC and 0.1% SDS; and then in 0.1×SSC and 0.1% SDS; and wherein expression of said isolated nucleic acid sequence is induced by high temperature stress, is derived from barley, and confers thermotolerance to a plant transformed therewith.

* * * * *

SEQUENCE LISTING

<160> NUMBER OF SEQ ID NOS: 2

<210> SEQ ID NO 1
<211> LENGTH: 291
<212> TYPE: PRT
<213> ORGANISM: Hordeum vulgare L. Haruna-nijyo

<400> SEQUENCE: 1

```
Met Ala Ala Pro Val Val Asp Ala Glu Tyr Leu Arg Gln Val Asp Arg
1               5                   10                  15

Ala Arg Arg Ala Phe Arg Ala Leu Ile Ala Ser Lys Gly Cys Ala Pro
            20                  25                  30

Ile Met Leu Arg Leu Ala Trp His Asp Ala Gly Thr Tyr Asp Val Asn
        35                  40                  45

Thr Arg Thr Gly Gly Ala Asn Gly Ser Ile Arg Tyr Glu Glu Glu Tyr
    50                  55                  60

Thr His Gly Ser Asn Ala Gly Leu Lys Ile Ala Ile Asp Leu Leu Glu
65                  70                  75                  80

Pro Ile Lys Ala Lys His Pro Lys Ile Thr Tyr Ala Asp Leu His Gln
                85                  90                  95

Leu Ala Gly Val Val Ala Val Glu Val Thr Gly Gly Pro Thr Val Glu
            100                 105                 110
```

```
Phe Ile Pro Gly Arg Arg Asp Ser Ser Val Cys Pro Arg Glu Gly Arg
        115                 120                 125

Leu Pro Asp Ala Lys Lys Gly Ala Pro His Leu Arg Asp Ile Phe Tyr
    130                 135                 140

Arg Met Gly Leu Thr Asp Lys Asp Ile Val Ala Leu Ser Gly Gly His
145                 150                 155                 160

Ser Leu Gly Lys Ala His Pro Glu Arg Ser Gly Phe Asp Gly Ala Trp
                165                 170                 175

Thr Arg Asp Pro Leu Lys Phe Asp Asn Ser Tyr Phe Leu Glu Leu Leu
            180                 185                 190

Lys Gly Glu Ser Glu Gly Leu Leu Lys Leu Pro Thr Asp Lys Ala Leu
        195                 200                 205

Leu Asp Asp Pro Glu Phe Arg Arg Tyr Val Glu Leu Tyr Ala Lys Asp
    210                 215                 220

Glu Asp Val Phe Phe Lys Asp Tyr Ala Glu Ser His Lys Lys Leu Ser
225                 230                 235                 240

Glu Leu Gly Phe Thr Pro Arg Ser Ser Gly Pro Ala Ser Thr Lys Ser
                245                 250                 255

Asp Val Ser Thr Ala Val Val Leu Ala Gln Ser Ala Val Gly Val Ala
            260                 265                 270

Val Ala Ala Ala Val Val Ile Ala Gly Tyr Leu Tyr Glu Ala Ser Lys
        275                 280                 285

Arg Ser Lys
    290

<210> SEQ ID NO 2
<211> LENGTH: 1089
<212> TYPE: DNA
<213> ORGANISM: Hordeum vulgare L. Haruna-nijyo

<400> SEQUENCE: 2
cttctagggt cgtccgcgat ggcggctccg gtggtggacg ccgagtacct gcgccaggtc      60
gacagggcgc gccgcgcctt ccgtgccctc atcgcctcca agggatgcgc ccccatcatg     120
ctccgcctcg catggcatga tgctggcacc tatgatgtga acacaagaac tggtggtgca     180
aatggttcaa ttagatacga ggaagagtac acccatggtt caaatgctgg cttaaaaatt     240
gctattgatc tccttgagcc tattaaagcg aagcatccaa agattacata tgcagacctt     300
catcagcttg ccggagtagt tgcagttgaa gtcaccgggg gtccaaccgt tgagttcatc     360
cctggaagac gtgattcgtc agtttgtccc cgtgaaggac gccttcctga tgctaagaaa     420
ggtgcaccac atctaaggga catctttat cgaatgggt taacagacaa agatattgta     480
gcactatctg gggggcacag cctgggaaag gcgcatcctg aaaggtctgg gtttgacggt     540
gcatggactc gtgaccctct gaaatttgac aactcatact tcttgagct actgaagggg     600 gaatctgagg gtcttctgaa gctccctact gataaggcat tgttggatga tcctgaattt     660
cgacgctatg tggagcttta tgcaaaggat gaggatgttt tcttcaagga ctacgctgaa     720
tcacacaaaa aacttctga acttggcttc acaccacgga gcagtggccc agcatctaca     780
aaatcagatg tttcaactgc tgttgtactt gcacagagtg cagtcggggt agcagttgct     840
gcagctgtag ttatcgcggg ctacctgtac gaagcttcca agaggagcaa gtaaggggtt     900
cgtgagttct tggatgacat tcccttattt agtaagtatc aagttattat tctaaaaaaa     960
```

```
taagtgccaa gtgcaaataa cagaactcta gtgatgaaca accaacagta gtctcaaaat    1020
atttcataca ttcttgagga catctccttc atatatatac atcatacttg aataaaaaaa    1080
aaaaaaaaa                                                            1089
```